(12) United States Patent
Luo et al.

(10) Patent No.: US 8,309,101 B2
(45) Date of Patent: Nov. 13, 2012

(54) PASTEURELLA MULTOCIDA VACCINE

(75) Inventors: Yugang Luo, Kalamazoo, MI (US); Paul Vermeij, St. Anthonis (NL); Antonius Arnoldus Christiaan Jacobs, Kessel (NL)

(73) Assignee: Intervet International B.V., Boxmeer (NL)

( * ) Notice: Subject to any disclaimer, the term of this patent is extended or adjusted under 35 U.S.C. 154(b) by 775 days.

(21) Appl. No.: 11/722,476

(22) PCT Filed: Dec. 21, 2005

(86) PCT No.: PCT/EP2005/056995
§ 371 (c)(1),
(2), (4) Date: Sep. 6, 2007

(87) PCT Pub. No.: WO2006/022586
PCT Pub. Date: Nov. 23, 2006

(65) Prior Publication Data
US 2010/0062017 A1    Mar. 11, 2010

Related U.S. Application Data

(60) Provisional application No. 60/639,447, filed on Dec. 22, 2004.

(51) Int. Cl.
*A61K 39/102*    (2006.01)
*A61K 39/015*    (2006.01)

(52) U.S. Cl. ............... 424/255.1; 424/268.1; 424/272.1

(58) Field of Classification Search ............... 424/268.2, 424/272.1; 435/258.2
See application file for complete search history.

(56) References Cited

U.S. PATENT DOCUMENTS 6,248,329 B1 *    6/2001    Chandrashekar et al. . 424/191.1

FOREIGN PATENT DOCUMENTS

| EP | 1350796 A1 * | 10/2003 |
| WO | WO/94/11024 * | 5/1994 |
| WO | 03086277 | 10/2003 |

OTHER PUBLICATIONS

Rhoades et al 1990 Journal of Avian Diseases pp. 381-383.*
Bowie et al (Science, 1990, 247:1306-1310).*
Ellis (Chapter 29 of Vaccines, Plotkin, et al. (eds) WB Saunders, Philadelphia, 1998, especially p. 571, paragraph 2).*
Database EMBL [Online], "*Pasteurella multocida* subsp. multocida str. Pm70 section 125 of 204 of the complete genome" XP002392876, EBI accession No. AE006158, Database accession No. AE006158, Feb. 10, 2001.
May, Barbara J. et al: "Complete genomic sequence of *Pasteurella multocida*, Pm70" Proceedings of the National Academy of Sciences of USA, National Academy of Science, Washington, DC, 98:6, pp. 3460-3465, Mar. 6, 2001.
Database EMBL [Online], "*Pasteurella multocida* subsp. multocida str. Pm70 section 125 of 204 of the complete genome" XP002392876, EBI Accession No. AE006158, Database Accession No. AE006158, dated Feb. 10, 2001.
May, Barbara J. et al., Complete genomic sequence of *Pasteurella multocida*, Pm70, Proceedings of the National Academy of Sciences of USA, National Academy of Science, Washington, DC, Mar. 13, 2011, vol. 98, No. 6, pp. 3460-3465.

* cited by examiner

*Primary Examiner* — Ram R Shukla
*Assistant Examiner* — Nina Archie
(74) *Attorney, Agent, or Firm* — William M. Blackstone

(57) ABSTRACT

The present invention relates to live attenuated bacteria of the species *Pasteurella multocida*, to live attenuated vaccines comprising such live attenuated bacteria, to the use of such bacteria for the manufacture of such vaccines, to methods for the preparation of such vaccines and to diagnostic tests for the detection of such bacteria.

7 Claims, 1 Drawing Sheet

Fig. 1 Cummulative mortality after challenge

—✳— P15 drinking water  —◆— controls  —▲— P15 aerosol

PASTEURELLA MULTOCIDA VACCINE

PRIORITY CLAIM TO RELATED PATENT APPLICATIONS

This patent claims priority under 35 U.S.C. §371 as a national phase of International Patent Application No. PCT/EP2005/056995 (filed Dec. 21, 2005; and published on Nov. 23, 2006 as International Publication No. WO 2006/122586), which, in turn, claims priority to U.S. Provisional Patent Application No. 60/639,447 (filed Dec. 22, 2004). The entire text of each of the above-referenced patent applications is hereby incorporated by referenced into this patent.

The present invention relates to live attenuated bacteria of the species Pasteurella multocida, to live attenuated vaccines comprising such live attenuated bacteria, to the use of such bacteria for the manufacture of such vaccines, to methods for the preparation of such vaccines and to diagnostic tests for the detection of such bacteria.

The Gram-negative bacterium Pasteurella multocida has been known as the causative agent of diseases in several animal species for over a century now. Pasteurella multocida is known i.a. to cause fowl cholera in poultry, haemorrhagic septicaemia in cattle and atrophic rhinitis in pigs. Additionally its importance as a human pathogen has become more and more clear over the last 60 years.

There is only one species of Pasteurella multocida. No subspecies exist. Nevertheless, a subdivision can be made on the basis of differences in capsular antigens and LPS antigen. Five Pasteurella multocida groups, A-E, have been defined based on capsular antigens and 16 somatic serotypes have been defined based on LPS antigen. The pathogenicity or virulence is not influenced by the capsular antigen group or the LPS serotype of the strains. The capsular antigen group merely determines the host animal of any specific strain.

Strains causing fowl cholera belong mainly to capsular antigen group A. Two kinds of disease are known: acute and chronic fowl cholera. Symptoms of acute fowl cholera are depression, ruffled feathers, fever, anorexia, mucosal discharge and increased respiratory rate. Lesions such as petechial and ecchymotic haemorrhages, general passive hyperemia and increased peritoneal and pericardial fluids are frequently seen.

Symptoms of disease in chronically infected birds are usually associated with localized infections. Swellings of the wattles, sinuses, periorbital subcutaneous tissues, legs or wing joints often occur. Exudative conjunctivitis and pharyngitis are also often seen. Lesions in chronically infected birds are generally characterized by fibri nosuppurative exudates, focal necrosis and connective tissue proliferation.

Strains causing haemorrhagic septicaemia in cattle and water buffaloes, but also in pigs, sheep, goats, deer and camels, belong mainly to the B and E capsular antigen group. Haemorrhagic septicaemia is an acute disease characterized by a rapid course, edematous swelling in the head -throat-brisket region, swollen and haemorrhagic lymph nodes and the presence of numerous sub serous petechial haemorrhages.

In pigs, Pasteurella multocida causes atrophic rhinitis and pneumonia. These syndromes are caused mainly by strains of capsular type A and D. Also cases of acute septicaemia have been described, which were caused by capsular type B. Clinical signs associated with atrophic rhinitis are sneezing, nasal discharge, shortening and twisting of the snout, pneumonia and growth retardation. Pneumonia is mainly seen as a secondary infection, increasing the severity of primary lesions. Clinical signs include a dry non -productive cough, which becomes productive, and in severe cases a rise in body temperature.

In principle, when it comes to vaccination against Pasteurella multocida, there are two approaches to protect against Pasteurella multocida infection: vaccination with killed vaccines (bacterins) and vaccination with live attenuated vaccines. Bacterins are economically attractive, because they are inexpensive to produce. They must however be injected, they often cause severe tissue reactions, a high challenge pressure can still cause disease outbreaks in bacterin-vaccinated animals and worst of all; they only give protection against the homologous serotype.

Contrary to this, vaccination with live attenuated vaccines gives a good cross -protection, not only against homologous serotypes but also against heterologous serotypes. Therefore these vaccines would appear to be the vaccines of choice, but there are two serious disadvantages connected with the use of live vaccines: in the first place the live attenuated Pasteurella multocida vaccine strains currently in use are ill -defined: the nature of their attenuated behavior is unknown. Therefore, there is always the risk of reversion to virulence.

And secondly, there have been outbreaks of pasteurellosis that could be attributed to the live vaccine strains used A possible reason for such outbreaks could be the reversion-to-virulence of the vaccine strain used or an insufficient level of attenuation.

Therefore, there clearly is a need for attenuated live Pasteurella multocida vaccines that are both efficacious and safe, such vaccines must provide protection against Pasteurella multocida infection or the effects thereof and at the same time behave attenuated without being prone to reversion to virulence.

It is an objective of the present invention to provide a live attenuated Pasteurella multocida strain that fulfills these requirements.

It was surprisingly found now, that a novel, hitherto unknown gene of Pasteurella multocida, further referred to as the Orf-15 gene can be deleted without impairing the immune reactivity of the strain, while at the same time dramatically decreasing the virulence of the bacterium. The presence of the gene in wild type Pasteurella multocida is not restricted to a specific capsular antigen group or somatic serotype. The gene is present in Pasteurella multocida strains regardless the capsular antigen group or somatic serotype: it is found in all 16 somatic serotypes and all five capsular antigen groups.

Therefore, the gene is a universal attenuation target in Pasteurella multocida, now for the first time allowing the preparation of safe vaccines for Pasteurella multocida-related disease. The approach is therefore equally suitable for the preparation of e.g. vaccines protecting humans against Pasteurella multocida infection or the effects thereof, vaccines protecting poultry against fowl cholera, vaccines protecting pigs against atrophic rhinitis and vaccines protecting cattle and water buffaloes against haemorrhagic septicaemia.

Moreover, it was found that live attenuated Pasteurella multocida strains missing the Orf-15 gene provide not only very good protection against their homologous serotype, but also a very good cross-protection against heterologous serotypes.

A first embodiment of the invention therefore relates to a live attenuated Pasteurella multocida bacterium that is not capable of expressing a functional Orf-15 protein. The sequence of the novel open reading frame Orf-15 gene is presented in SEQ ID NO: 1, and the Orf-15 protein it encodes is depicted in SEQ ID NO: 2.

A functional Orf-15 protein is understood to be a Orf-15 protein capable of causing full virulence as in wild type *Pasteurella multocida*.

Therefore, a *Pasteurella multocida* strain that is defective in at least this capability is considered to be not capable of expressing a functional Orf-15 protein. Any mutation, such as an insertion replacement or deletion mutation, in the Orf-15 gene that leads to a decrease of virulence when compared to the wild type *Pasteurella multocida* strain is considered to fall within the scope of the present invention.

A decrease in virulence of a strain for the purpose of this invention is defined in two ways. One definition of a decrease in virulence relates to the level of protection against lethal infection: it is known that infection of turkeys with a *Pasteurella multocida* wild type strain under controlled conditions gives a mortality of above 50% (see i.a. Example section). A *Pasteurella multocida* strain with decreased virulence due to a mutation in the Orf-15 gene according to the invention is a strain that under the same conditions gives a level of mortality below 10%.

The other definition of a decrease in virulence relates to the level and the seriousness of lesions after vaccination, when compared to sub-lethal infection with a wild type *Pasteurella multocida* strain. Thus, according to the second definition of decrease in virulence, a *Pasteurella multocida* strain has a decreased level of virulence if it causes a level of lesions that is below 30% of the level of lesions caused by infection with a wild type *Pasteurella multocida* strain.

Thus a *Pasteurella multocida* strain is considered to fall within the scope of the present invention if it has e.g a mutation in the Orf-15 gene or an agent interfering with the expression of the protein encoded by the Orf-15 gene (see below) that leads to a decrease in virulence according to at least one of the two definitions of decrease in virulence provided above.

Such a mutation can be an insertion, a deletion, a substitution or a combination thereof, provided that the mutation leads to the failure to express a functional Orf-15. (It goes without saying that a silent mutation such as a mutation of codon CTC to CTT does not affect the Orf-15 protein and therefore does not lead to a failure to express a functional Orf-15 protein. Therefore, for the purpose of the present invention such a mutation is not considered).

Usually, a mutation will be an insertion, a replacement or a deletion of one or more nucleotides. Especially the insertion or deletion of a number of nucleotides that is not dividable by three lead s to a frame-shift, which in turn leads to a nonsense code. As a result, a truncated Orf-15 protein will be synthesized that has a decreased functionality or even no functionality at all.

There are many ways known in the art for introducing a mutation in an open reading frame. One possible way of obtaining such mutations is by means of classical methods such as the treatment of wild-type bacteria with mutagenic agents such as base analogues, treatment with ultraviolet light or temperature treatment. Selection of Orf-15 mutants would however be quite a time-consuming task.

Moreover, the nature of the mutation caused by classical mutation techniques would be unknown. This might be a point mutation in the Orf-15 gene that could eventually revert to wild-type. In order to avoid this small risk, transposon mutagenesis would be a good alternative. Making mutants by transposon mutagenesis is also a technique well-known in the art. This is a kind of mutation accomplished at a localized site in the chromosome. Stable, avirulent, immunogenic, transposon-mediated mutants of *P. multocida* can be thus be produced. Transposon-mediated mutants are those that have the transposon inserted into the bacterial genome.

A "transposon" is a DNA element that can insert into DNA molecules by transposition, a non-homologous recombination process that does not require extensive DNA sequence homology.

Transposons usually include genes encoding transposition enzymes called transposases, which cut the DNA at the end of the transposons and insert the transposons into the target DNA. In addition, transposons usually contain marker genes encoding antibiotic resistance, which can be used for selection of the mutants with transposon insertions. Known transposons include Tn3, Tn5, TnphoA, Tn7, Tn9, Tn10 and functional fragments thereof (*Mobile DNA*, eds. D. E. Berg and M. M. Howe, ASM Press, 1989). Merely as an example; Tn10 transposon are very well known in the art and des cubed i.a. by Lee (Lee, M. D., Henk, A. D., Veterinary Microbiology, 50, 1996, 143 -1480). A transposon insertion mutant can be produced by standard methods known to those skilled in the art (Mobile DNA, eds. D. E. Berg and M. M. Howe, ASM Press, 1989).

The selection for Orf-15 transposon mutations would be easier and less time consuming, due to the fact that a PCR using primers located at the 3'-terminal and 5'-terminal side of the Orf-15 gene would directly show if the transposon -insertion is located in the Orf-15 gene or elsewhere.

An even more elegant possibility to introduce a mutation into Orf-15, now at a predetermined site, rather deliberately than randomly, is offered by recombinant DNA-technology, more specifically site-directed mutagenesis. Such a mutation may again be an insertion, a deletion, a replacement of one nucleotide by another one or a combination thereof, with the only proviso that the mutated gene no longer encodes functional Orf-15. Such a mutation can e.g. be made by deletion of a number of base pairs. Even very small deletions such as single base pair deletions leading to frame shift can sufficiently render Orf-15 non-functional. More preferably, a longer stretch is removed, e.g. 10, 50 or more base pairs. Even more preferably, the who le Orf-15 gene is deleted.

Techniques for the construction of Orf-15-negative mutants through site-directed mutagenesis are well-known standard techniques. They relate e.g. to cloning of the Orf-15 gene, modifying the gene sequence by site-directed mutagenesis, restriction enzyme digestion followed by re-ligation or PCR-approaches and to subsequent replacement of the wild type Orf-15 gene with the mutant gene (allelic exchange or allelic replacement). Standard recombinant DNA techniques such as cloning of the Orf-15 gene in a plasmid, digestion of the gene with a restriction enzyme, followed by endonuclease treatment, re-ligation and homologous recombination in the host strain, are all known in the art and described i.a. in Maniatis/Sambrook (Sambrook, J. et al. Molecular cloning: a laboratory manual. ISBN 0-87969-309-6). Site-directed mutations can e.g. be made by means of in vitro site directed mutagenesis using the TRANSFORMER® kit sold by Clontech. PCR-techniques are extensively described in (Dieffenbach & Dreksler; PCR primers, a laboratory manual. ISBN 0-87969-447-3 and ISBN 0-87969-447-5).

The most common methods for the construction of a live attenuated *Pasteurella multocida* bacterium that is not capable of expressing a functional Orf-15 protein rely, as explained above, on mutations in the Orf-15 gene. However there is an alternative way of making live attenuated *Pasteurella multocida* bacteria that are not capable of expressing a functional Orf-15 protein. This alternative way relates to interaction with the messenger RNA encoding the Orf-15 protein. Expression of a protein is a two -step process, comprising the step of generating Orf-15 mRNA through transcription of the DNA and the subsequent step of translation of this mRNA into the Orf-15 protein. The presence of certain types of RNA such as e.g. Orf-15-specific dsRNA, Orf-15-specific short interfering RNA or Orf-15-specific anti-sense RNA in the bacterium would interfere with the Orf-15 mRNA, and therefore block the translation of Orf-15 mRNA into wild-type amounts of Orf-15 protein. The RNAs upon which this mechanism is based or the mechanism as such, is commonly known as RNAi. Therefore, the presence of e.g. Orf-15-specific siRNA, dsRNA or Orf-15-specific anti-sense RNA would have the same effect as a mutation in the Orf-15 gene: such a bacterium would not be capable to express a functional Orf-15 protein.

The use of anti-sense RNA for the silencing of genes has been known for a few decades already, and the use of RNAi (e.g. dsRNA or siRNA), commonly in use for about five years now, is also a well-established technique well-known in the art. Reviews on this topic have been written by Hannon, G. J. in Nature 418: 244 -251 (2002) and by Deni, A. M. and Hannon, G. J. in TRENDS in Biochemical Sciences 28: 196-201 (2003). Other papers, describing the use of siRNA in gene silencing are by Bertrand, J. R. et al., in B.B.R.C. 296: 1000-1004 (2002) and by Sorensen, D. R. et al., in J. Mol. Biol. 327: 761-766 (2003). The use of RNAi for the silencing of viruses in mammals has recently been suggested and has been reviewed i.a. by Quan-Chu Wang et al., (World J. Gastroenterol. 9: 1657 -1661 (2003)).

Generally spoken, the skilled person would possibly have a slight preference for the first approach; making a mutation in the Orf-15 gene. This is due to the fact that mutation of a gene, contrary to any RNA -interference based method, does not bring any additional genetic material into the cell.

Therefore, a preferred form of this embodiment relates to a live attenuated bacterium that is not capable to express a functional Orf-15 protein due to a mutation in the Orf-15 gene.

A deletion or insertion, especially an out-of-frame mutation will have a drastic effect on the functionality of the Orf-15 protein.

Therefore, in a more preferred form of this embodiment the mutation comprises an insertion and/or a deletion. In a most preferred form, the whole Orf-15 gene or at least its coding sequence is deleted.

The Orf-15 gene comprises a coding sequence as well as a promoter region and a ribosome binding site. The promoter site comprises at least the region comprising nucleotide 22 -71 of SEQ ID NO: 1, whereas the ribosome binding site spans nucleotides 92 -96. Therefore it goes without saying that any mutation rendering the promote r or ribosome binding site ineffective, and thus resulting in decreased expression or non-expression of Orf-15 is also considered to fall within the scope of the present invention.

Given the large amount of vaccines administered nowadays to both pets and farm animals, it is clear that combined administration of several vaccines would be desirable, if only for reasons of decreased vaccination costs. It is therefore very attractive to use live attenuated bacteria as a recombinant carrier for heterologous genes, encoding antigens selected from other pathogenic micro-organisms or viruses. Administration of such a recombinant carrier has the advantage that immunity is induced against two or more diseases at the same time. The live attenuated bacteria according to the present invention provide very suitable carriers for heterologous genes, due to their attenuated behavior.

Therefore, an even more preferred form of this embodiment relates to a live attenuated bacterium according to the invention that carries a heterologous gene encoding one or more antigens selected from the group of microorganisms and viruses pathogenic to humans and/or animals.

The use of the Orf-15 gene as an insertion site for a heterologous gene has the additional advantage that at the same time the Orf-15 gene is inactivated and the newly introduced heterologous gene can be expressed (in concert with the homologous bacterial genes).

Therefore, a still even more preferred form of this embodiment relates to a live attenuated *Pasteurella multocida* bacterium according to the invention that has as a characteristic that the heterologous gene is inserted in the gene encoding Orf-15.

The heterologous gene may carry a homologous promoter or any other promoter that is recognized by *Pasteurella multocida* RNA polymerase. The native Orf-15 promoter can also be used. This could be most easily arranged by deleting the ORF-15 coding sequence and replacing it by the heterologous gene of choice.

The construction of such recombinant carriers can be done routinely, using standard molecular biology techniques as described above.

In one most preferred form of this embodiment, the heterologous gene encodes one or more antigens selected from the group of porcine pathogens, consisting of Porcine Reproductive Respiratory Syndrome (PRRS) virus, Pseudorabies virus, Porcine Influenza virus, Porcine Parvovirus, Transmissible Gastroenteritis virus, rotavirus, Porcine Circovirus 1 or 2, *Escherichia coli, Erysipelothrix rhusiopathiae, Bordetella bronchiseptica, Haemophilus parasuts, Mycoplasma hyopneumoniae* and *Streptococcus suis*.

In another most preferred form of this embodiment, the heterologous gene encodes one or more antigens selected from the group of cattle pathogens, consisting of Bovine Herpesvirus, bovine Viral Diarrhoea virus, Parainfluenza type 3 virus, Bovine Paramyxovirus, Foot and Mouth Disease virus, *Pasteurella haemolytica, Staphylococcus aureus, Escherichia colt, Staphylococcus uberis*, Bovine Respiratory Syncytial Virus, *Theileria parva, Theileria annulata, Babesia bovis, Babesia bigemina, Babesia major, Trypanosoma species, Anaplasma marginale, Anaplasma centrale* or *Neospora caninum*.

In again another most preferred form of this embodiment, the heterologous gene encodes one or more antigens selected from the group of poultry pathogens, consisting of Fowlpox virus, Infectious Bronchitis virus, Infectious Bursal Disease (Gumboro), Marek's Disease Virus, Chicken Anaemia agent, Avian Reovirus, *Mycoplasma gallisepticum*, Turkey Rhinotracheitis virus, *Haemophilus parag allinarum* (Coryza), Chicken Poxvirus, Avian Encephalomyelitisvirus, Duck Plague virus, Newcastle Disease virus, Egg Drop syndrome virus, Infectious Laryngotracheitis virus, Herpes Virus of Turkeys, Eimeria species, *Ornithobacterium rhinotracheale, Mycoplasma synoviae, Clostridium perfringens, Salmonella* species and *E. coli*.

Another attractive possibility is to insert, preferably in the Orf-15 gene a gene encoding a protein involved in triggering the immune system, such as a cytokine, an interleukin or an interferon, or another gene involved in immune-regulation.

Because of their unexpected attenuated but immunogenic character in vivo, the bacteria according to the invention are very suitable as a basis for live attenuated vaccines.

Thus, another embodiment of the present invention relates to a live attenuated vaccine for the protection of animals or humans against *Pasteurella multocida* infection or the pathogenic effects thereof, that comprises a live attenuated bacterium according to the invention and a pharmaceutically acceptable carrier.

Such vaccines comprise an immunogenically effective amount of a live attenuated bacterium according to the invention. Immunogenically effective means that the amount of live attenuated bacteria administered at vaccination is sufficient to induce in the host an effective immune response against virulent forms of the bacterium.

In addition to an immunogenically effective amount of the live attenuated bacterium described above, a vaccine according to the present invention also contains a pharmaceutically acceptable carrier. Such a carrier may be as simple as water, but it may e.g. also comprise culture fluid in which the bacteria were cultured. Another suitable carrier is e.g. a solution of physiological salt concentration.

The useful dosage to be administered will vary depending on the age, weight and animal vaccinated, the mode of administration and the type of pathogen against which vaccination is sought. The Examples below give an example of suitable dosages. The skilled artisan is able to extrapolate these figures to other animal species.

The vaccine may comprise any dose of bacteria sufficient to evoke an effective immune response. Doses below $10^2$ live attenuated bacteria may not always be successful to sufficiently stimulate the immune system and doses above $10^{10}$ live attenuated bacteria are not very attractive from an economical point of view.

Doses ranging between $10^3$ and $10^9$ bacteria are usually very suitable doses.

Optionally, one or more compounds having adjuvant activity may be added to the vaccine.

A live attenuated *Pasteurella multocida* bacterium according to the invention does not necessarily need such an adjuvant for efficacy, but especially for combination vaccines comprising a live attenuated *Pasteurella multocida* bacterium according to the invention and antigenic material from another pathogenic virus or microorganism (see below) it could be worthwhile to add an adjuvant.

Adjuvants are non-specific stimulators of the immune system. They enhance the immune response of the host to the vaccine. Examples of adjuvants known in the art are Freund's Complete and Incomplete adjuvant, vitamin E, non-ionic block polymers, muramyl dipeptides, ISCOMs (immune stimulating complexes, cf. for instance European Patent EP 109942), Saponins, mineral oil, vegetable oil, and CARBOPOL.

Adjuvants, specially suitable for mucosal application are e.g. the *E. coli* heat-labile toxin (LT) or *Cholera* toxin (CT).

Other suitable adjuvants are for example aluminum hydroxide, aluminum phosphate or aluminum oxide, oil-emulsions (e.g. of BAYOLF® or MARCOL52®, saponins or vitamin-E solubilisate.

The use of such adjuvants is especially preferred if other, viral or subunit vaccines are added, e.g in the case of a *Pasteurella multocida* combination vaccine.

Therefore, in a preferred form of this embodiment, the live attenuated vaccine according to the present invention comprises an adjuvant.

Other examples of pharmaceutically acceptable carriers or diluents useful in the present invention include stabilisers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Especially when such stabilisers are added to the vaccine, the vaccine is very suitable for freeze-drying. Freeze-drying has the advantage that the freeze-dried material does not require specialized storage conditions such as storage below −20 or even −80 degrees Celsius. Therefore, in a more preferred form of this embodiment, the live attenuated vaccine is in a freeze-dried form.

In a vaccine comprising a bacterium according to the invention as described above, it is beneficial to include antigens derived from another micro-organism or a virus pathogenic to humans or animals or an antibody against such an antigen.

There are several ways of obtaining such a vaccine. One easily applicable approach is the admixing of a live attenuated *Pasteurella multocida* strain according to the invention with one or more antigens of other human or animal pathogens and a pharmaceutically acceptable carrier.

Thus, an even more preferred form of this embodiment relates to a live attenuated vaccine according to the invention, that is characterized in that it additionally comprises one ore more antigens selected from the group of viruses and micro-organisms pathogenic to humans and/or animals.

Preferably, such antigens are selected from the group of porcine, bovine or poultry pathogens described above.

Again another embodiment of the invention relates to live attenuated bacterium according to the invention for use in a vaccine.

Still another embodiment of the invention relates to the use of a live attenuated bacterium according to the invention for the manufacture of a vaccine for the protection of humans or animals against infection with a *Pasteurella multocida* bacterium or the pathogenic effects of infection.

For administration to animals or humans, the vaccine according to the present invention can be given inter alia intranasally, intradermally, subcutaneously, orally, by aerosol or intramuscularly.

For application to poultry, oral (drinking water), spraying and eye-drop administration are especially suitable, if only for the ease of such routes of administration.

The skilled person would know how to administer a vaccine according to the invention, because the method would not differ significantly from the methods followed for vaccination with presently existing *Pasteurella multocida* vaccines, especially live attenuated *Pasteurella multocida* vaccines. A vaccine according to the invention, especially when used for poultry, would preferably be given orally through drinking water or by spraying.

Still another embodiment of the invention relates to methods for the preparation of a vaccine according to the invention. Such methods comprise the admixing of a live attenuated bacterium according to the invention and a pharmaceutically acceptable carrier.

Given the fact that diseases caused by *Pasteurella multocida* are in most cases highly contagious, it would be highly beneficial to have a quick and easy tool, a diagnostic test, for the early detection of *Pasteurella multocida* infection in animals.

Such diagnostic tests should be both quick and selective, in the sense that they must provide early detection and they must be specific for *Pasteurella multocida* and not give false positive reactions with other bacteria, regardless of whether those other bacteria belong to other *Pasteurella* species or non-*Pasteurella* species.

Diagnostic tests based upon the presence or absence of antibodies against *Pasteurella multocida* although often reliable, are not very attractive if an early detection of the bacteria is needed. This is due to the fact that the development of antibodies in the infected animal against *Pasteurella multocida* may easily take up to two weeks.

Therefore it is another objective of this invention to provide diagnostic tools suitable for both early and specific detection of *Pasteurella multocida* infection.

It was surprisingly found now, that the Orf-15 gene sequence is unique for *Pasteurella multocida*, and is not present in other *Pasteurellaceae*.

Therefore, another embodiment relates to RNA- or DNA-based tests for the detection of *Pasteurella multocida*.

A diagnostic test for the detection of *Pasteurella multocida* is e.g. based upon the reaction of DNA or RNA isolated from the animal to be tested, with specific probes or it is e.g. a (RT-)PCR test based upon the Orf-15 gene sequence or based upon nucleic acid sequences that are complementary to that sequence. If nucleic acid molecules specific for the *Pasteurella multocida* associated proteins according to the invention are present in the animal, these will e.g. specifically bind to specific PCR-primers and will subsequently become amplified in (RT-)PCR-reaction. The PCR-reaction product can then easily be detected in DNA gel electrophoresis. (RT-) PCR reactions are well-known in the art (see reference below). The nucleic acid molecules can most easily be isolated from affected tissue of body fluids of the animal to be tested.

In pigs, a nasal swab of material from affected lung tissue pro vides suitable material for (RT-) PCR testing. Trachea swabs or material from affected liver, lung or heart tissue would be the preferred source in chickens. In buffalo, sheep and cattle the organs of choice would be the nose and affected lung tissue.

Standard PCR-textbooks give methods for determining the length of the primers for selective PCR-reactions with nucleic acid molecules specific for the Orf-15 gene according to the invention. Primers with a nucleotide sequence of at least 12 nucleotides are frequently used, but primers of more than 15, more preferably 18 nucleotides are somewhat more selective. Especially primers with a length of at least 20, preferably at least 30 nucleotides are very generally applicable. PCR-techniques are extensively described in (Dieffenbach & Dreksler; PCR primers, a laboratory manual. ISBN 0-87969-447-5 (1995)).

Nucleic acid molecules of the Orf-15 gene or parts of those nucleic acid molecules having a length of at least 12, preferably 15, more preferably 18, even more preferably 20, 22, 25, 30, 35 or 40 nucleotides in that order of preference or nucleic acid molecules complementary therewith are therefore also part of the invention. Such nucleic acid molecules can e.g. be used as primers in (RT-)PCR-reactions in order to enhance the amount of nucleic acid that encodes the proteins according to the invention. This allows the quick amplification of specific nucleotide sequences for use as a diagnostic tool for e.g. the detection of *Pasteurella multocida* in tissue as indicated above.

Both PCR-reactions and hybridisation reactions are well-known in the art and are i.a. described in Maniatis/Sambrook (Sambrook, J. et al. Molecular cloning: a laboratory manual. ISBN 0-87969-309-6).

Thus, another embodiment of the invention relates to a diagnostic test for the detection of *Pasteurella multocida* associated DNA or RNA, wherein that test has as a characteristic feature that it comprises a nucleic acid molecule having a nucleic acid sequence as depicted in SEQ ID NO: 1 or a nucleic acid molecule that is complementary to said nucleic acid sequence, or a fragment thereof having a length of at least 12, preferably at least 15, more preferably at least 18 nucleotides.

EXAMPLES

Example 1

Selection of Spontaneous Nalidixic Acid Resistant Mutant of P-1059.

A *Pasteurella multocida* strain, P-1059 (ATCC Number 15742, American Type Culture Collection, Manassas, Va., USA), was cultured in Luria-Bertani (LB) broth at 37° C. overnight. 0.2 ml of the culture was spread onto LB agar plates containing nalidixic acid 10 mg/ml and incubated at 37° C. for 48 hours. A couple of resistant colonies were picked and streaked onto nalidixic acid containing LB agar plates again. After another 48 hours incubation, one resistant colony was picked and inoculated into 10 ml LB broth containing 20 mg/ml of nalidixic acid and cultured overnight. The culture was mixed with 5 ml of glycerol, aliquoted into 1.8 ml tubes (1 ml per tube) and stored at −70° C. The nalidixic resistant strain was designated P-1059NR.

Example 2

Selection of Spontaneous thyA-Mutant of P-1059NR

P-1059NR was cultured in LB broth containing 20 mg/ml of nalidixic acid and 10 mg/ml of thymine at 37° C. overnight. 0.2 ml of the culture was spread onto a LB plate containing 20 mg/ml of nalidixic acid, 10 mg/ml of trimethoprim and 50 mg/ml of thymine, and incubated at 37° C. for 24-48 hours. Ten colonies were transferred to the same kind of plate and the LB plate containing only 20 mg/ml of nalidixic acid and 10 mg/ml of trimethoprim. The colonies that grew on the first plate but not the second plate were thyA-mutants. One of the thyA-mutants was inoculated into 10 ml of LB broth containing 20 mg/ml of nalidixic acid, and 150 mg/ml of thymine, and incubated at 37° C. overnight. The culture was mixed with 5 ml of glycerol, aliquoted 1 ml per tube and stored at −70° C. The stored thyA-mutant was designated P9818.

Example 3

Construction of Tn Vector pYL1.3

The *E. coli thyA* gene was amplified by polymerase chain reaction (PCR) from genomic DNA of *E. coli* K-12 with primers of 5'-AAGCTTGGCTGTCTCAGGTTTGTTCC-3' [SEQ ID NO.: 3] and 5'-TAGCTTGGCCAGTTTC-TATTTCTTCG-3' [SEQ ID NO.: 4]. The PCR fragment was trimmed with T4 DNA polymerase plus dGTP. pLOF/Ptt (Herreno, M., de Lorenzo, V. Timmis, K.N., *J. Bacteriology*, 172, 1990, 6557-6567) was digested with Xba I and Sf to remove the Ptt gene and was partially filled with Klenow enzyme and dCTP. The trimmed PCR fragment (one end) was ligated to partially filled Xba I end of the digested plasmid. Another end of the PCR fragment and Sfi end of the digested plasmid were blunted with T4 DNA polymerase and dNTP. This treated plasmid with the ligated PCR fragment was self-ligated and transformed into *E. coli* SM 10. One transformant containing the right sized plasmid was purified, cultured aliquoted and stored at −70° C. The plasmid in this transformant was designated pYL1.3.

Example 4

Construction of *P. multocida* Tn Mutants Library

P9818 was cultured in LB broth+200 mg/ml of thymine at 37° C. with vigorous shaking for about 48 hours. *E. coli* SM10 containing pYL1.3 was cultured in LB broth overnight. 0.1 ml of P9818 and *E. coli* SM 10 culture was mixed, spread onto LB+(IPTG 100 mg/ml+10 mM MgSO4+thymine 200 mg/ml) and incubated at 37° C. overnight. The bacterial lawn was washed from the plates and collected. 0.1 ml of the collected suspension was spread onto LB plates+nalidixic acid 20 mg/ml and incubated at 37° C. for 48 hours. About 150 transconjugants were picked up and restreaked onto LB plates+na lidixic acid 20 mg/ml for purification. These transconjugants were cultured in LB broth+nalidixic acid 20 mg/ml and stored at −70° C. These transconjugants were restreaked simultaneously onto LB plates+nalidixic acid 20 mg/ml and LB plates+nalidixic acid 20 mg/ml+ampicillin 25 mg/ml to select transposon mutants. The transconjugants (about 120) which grew only on LB plates+nalidixic acid 20 mg/ml were recultured in LB broth+nalidixic acid 20 mg/ml, aliquoted and stored at −70° C.

Example 5

Characterization (Southern Blot) of the Transposon Mutants

A number of 17 Tn mutants were randomly picked and cultured in LB broth+nalidixic acid 20 mg/ml. Genomic DNAs of the mutants were extracted using a QIAMP kit (QIAGEN Inc., Valencia, Calif., USA). The DNAs were digested with *Hind III*. P-1059 genomic DNA digested with *Hind III*, pGP704 (Herreno, M., de Lorenzo, V. Timmis, K.N., *J. Bacteriology*, 172, 1990, 6557-6567) and pYL1.3 were also included as controls. A Southern blot was performed by standard methods (Sambrook, et al., eds., Molecular Cloning, $2^{nd}$ Edition, Cold Springs Harbor Laboratory Press, Plainview, N.Y., 1989). A DIG DNA labeling and Detection Kit (Roche Molecular Biochemicals, Indianapolis, Ind., USA) was used for the probe labeling and Southern blot. The pGP704 and PCR amplified *E. coli thyA* gene were labeled with digoxigenin, and the digested genomic DNAs were probed according to the manufacturer's instructions. The results showed most of the mutants were transposition mutants with one Tn insertion and a few of the mutants were plasmid integration mutants.

The transposon mutants thus obtained were checked for their attenuated behavior in standard animal tests.

Of those transposon mutants that behaved attenuated, the insertion site of the transposon was identified and the disrupted gene was sequenced.

One of the transposon mutants found is depicted *Pasteurella multocida* strain P15 (shortly strain P15). This mutant has the transposon inserted in Orf-15. It is this strain that has been used for vaccination experiments in the next Example.

Example 6

Vaccination Experiments

In these experiments, the vaccination was done together with vaccination against Newcastle disease. This was done because vaccination with a *Pasteurella multocida* vaccine and a Newcastle disease vaccine would in the veterinary practice preferably be done at the same day, even at the same moment. The advantage of the experimental approach described here is therefore that it additionally gives an impression about the behaviour of the vaccine under field conditions.

PM Vaccine Cultures

Fresh cultures of *Pasteurella multocida* strain P15 in TPB were used for aerosol vaccination. The infectivity titter was determined immediately after use. The *Pasteurella multocida* strain P15 cultures use for priming comprised $1.5 \times 10^8$ CFU/ml and the cultures used for the booster comprised $1.6 \times 10^9$ CFU/ml.

For administration in drinking water 500 ml of each culture was centrifuged, and the pellet was dissolved in 500 ml skim milk-solution. The *Pasteurella multo cida* strain P15 culture used for priming comprised $1.2 \times 10^8$ CFU/ml and the culture used for the booster comprised $1.3 \times 10^9$ CFU/ml.

ND Cultures

ND vaccine cultures contained 7.3 $EID_{50}$ (Egg Infectious Doses) per dose per bird.

Turkeys were given water and fed ad libitum.

Grouping and Dosing

TABLE 1

Treatment scheme

| no. of birds | vaccination at day 14 and 28 | no. of birds chall. with virulent P.m. at day 42 |
|---|---|---|
| 25 | P15 aerosol + ND vaccine | 15 |
| 25 | P15 drinking-water + ND vaccine | 16 |
| 25 | ND vaccine | 15 |

Vaccination

See table 1 for the treatment scheme. All birds were spray vaccinated with ND vaccine using a spray can. Vaccination with strain P15 was done by aerosol using a paint sprayer (the birds remained in the aerosol for 10 minutes with the air circulation close d) or by drinking water. For drinking water vaccination 500 ml fresh culture was centrifuged and resuspended in 500 ml 2% skim milk (20 g skim milk/litre water). Water was withhold from the turkeys for at least 6 hours before vaccination. 500 ml vaccine culture was given in a water/drinking tower. After vaccination normal drinking water was applied as usual.

*Pasteurella Multocida* Challenges

Challenge was done by intra-muscular injection (1.0 ml, breast) of a fresh diluted culture of a wild-type *Pasteurella multocida* strain of serotype 1 containing $1.5 \times 10^5$ CFU/ml. The challenge culture was prepared in TPB as a fresh 5 hours cultures.

Mortality was recorded daily during 7 days. From birds that died and all other birds at 7 days post challenge, an attempt was made to isolate *P. multocida* from the liver.

Statistical Analysis

Mortality was compared using the Fischer exact test (Statistix for Windows, version 2.0).

TABLE 2

Summary results after vaccination

| Vaccine group | Mortality |
|---|---|
| P15 aerosol | 2/25 |
| P15 drinking water | 0/25 |
| Controls | 0/25 |

TABLE 3

Summary results after challenge.

| Vaccine group | Mortality | Reisolation of vaccine strain |
|---|---|---|
| P15 aerosol | 0/15 | 0/15 |
| P15 drinking water | 3/16 | 3/16 |
| Controls | 15/15 | 15/15 | bold: significantly different from controls

Results and Discussion

The post-vaccination observations are summarized in Table 2. After the vaccinations and before challenge 2 birds died in the P15 aerosol group, 0 in the P15 drinking water group and 0 in the control group. This mortality was probably related to the vaccine strains since no mortality was found in the control group. The post-mortems after vaccination showed that the aerosol route induced slightly more abnormalities (mild airsac lesions that could be due to the vaccine strains) compared to the drinking water group.

The post-challenge observations are summarised in Table 3 and FIG. 1. After a lethal heterologous challenge (1000× $LD_{50}$), various levels of protection were found. The aerosol vaccination route appeared to be the most efficacious route (100%), followed by the drinking water route (81%).

From the results it can be concluded that *Pasteurella multocida* Orf-15 mutants according to the invention are very suitable strains for use as a live attenuated strain in vaccines. The mortality observed after vaccination was with the highest dose possible (>$10^9$CFU/ml).

It should be kept in mind, that both the vaccination dose and the challenge dose used in this experiment are high. The vaccine dose can be strongly reduced until a level that no mortality or signs are observed. Also the challenge dose (1000×$LD_{50}$) can be strongly reduced.

Conclusion

From the results it can be concluded that *Pasteurella multocida* Orf-15 mutants according to the invention provide a very good basis for efficacious and safe live attenuated *Pasteurella multocida* vaccines.

Legend To The Figures

FIG. 1. This figure shows a comparison of the cumulative mortality of vaccinated animals (vaccination through drinking water and aerosol vaccination) versus control animals after challenge.

The invention claimed is:

1. A live, attenuated *Pasteurella multocida* bacterium strain, said bacterium having a transposon inserted within the Orf-15 gene, and thereby not being capable of expressing a functional Orf-15 protein, wherein said Orf-15 gene comprises SEQ ID NO: 1.

2. The live, attenuated *Pasteurella multocida* bacterium strain of claim 1 that does not comprise a protein having a sequence of SEQ ID NO: 2.

3. A live, attenuated vaccine for the protection of an animal against *Pasteurella multocida* infection or the pathogenic effects thereof, wherein said vaccine comprises an immunogenically protective amount of a live, attenuated bacterium according to claim 2 and a pharmaceutically acceptable carrier.

4. The live, attenuated vaccine according to claim 3, comprising an adjuvant.

5. The live, attenuated vaccine according to claim 3, wherein it is in a freeze-dried form.

6. The live, attenuated bacterium according to claim 2, having a mutation in the region comprising nucleotides 22-71 or 92-96, or both, of SEQ ID NO.: 1.

7. The live, attenuated bacterium according to claim 1, wherein the bacterium is *Pasteurella multocida* strain P15.

* * * * *

SEQUENCE LISTING

```
<160> NUMBER OF SEQ ID NOS: 2

<210> SEQ ID NO 1
<211> LENGTH: 476
<212> TYPE: DNA
<213> ORGANISM: Pasteurella multocida
<220> FEATURE:
<221> NAME/KEY: CDS
<222> LOCATION: (102)..(476)

<400> SEQUENCE: 1
caaggcaaag gcggattttt tattttaatc tgaatacaag gtacccattg tatattctct         60
gattatccca gtgggtttcc aatttaatga caggagcgtt t atg cat ata atc aaa      116
                                             Met His Ile Ile Lys
                                               1               5 acc tta atc tct gtt ggc gta gca ttt tca ctc agt gct tgc ctg agt        164
Thr Leu Ile Ser Val Gly Val Ala Phe Ser Leu Ser Ala Cys Leu Ser
                10                  15                  20 ctg gaa ggc gtt gaa ata gcg ggc tta gaa gga aaa tcc tct ggc aca        212
Leu Glu Gly Val Glu Ile Ala Gly Leu Glu Gly Lys Ser Ser Gly Thr
            25                  30                  35 tta acc aaa tat cgt tgt gaa aat ggc tat aaa gcc tct ata aaa caa        260
Leu Thr Lys Tyr Arg Cys Glu Asn Gly Tyr Lys Ala Ser Ile Lys Gln
        40                  45                  50 cgc gat aat ggt gtg gta agt atc gct ttc aat gat ggc aaa gac agc        308
Arg Asp Asn Gly Val Val Ser Ile Ala Phe Asn Asp Gly Lys Asp Ser
    55                  60                  65 tat gtc agc tac tta aat cat gtg cct tcc gct tcg gga acg ctg tat        356
Tyr Val Ser Tyr Leu Asn His Val Pro Ser Ala Ser Gly Thr Leu Tyr
70                  75                  80                  85 gtc aat gat aaa aat act tta aaa tgg cat cag aaa aat aat att gca        404
Val Asn Asp Lys Asn Thr Leu Lys Trp His Gln Lys Asn Asn Ile Ala
                90                  95                 100 gta ttt acc tac cca gat cgc aac tat gca aaa acg ggg caa tta gtg        452
Val Phe Thr Tyr Pro Asp Arg Asn Tyr Ala Lys Thr Gly Gln Leu Val
            105                 110                 115 aca aca aac tgt cat aag tat taa                                        476
Thr Thr Asn Cys His Lys Tyr
        120

<210> SEQ ID NO 2
<211> LENGTH: 124
<212> TYPE: PRT
```

-continued

```
<213> ORGANISM: Pasteurella multocida

<400> SEQUENCE: 2

Met His Ile Ile Lys Thr Leu Ile Ser Val Gly Val Ala Phe Ser Leu
1               5                   10                  15

Ser Ala Cys Leu Ser Leu Glu Gly Val Glu Ile Ala Gly Leu Glu Gly
                20                  25                  30

Lys Ser Ser Gly Thr Leu Thr Lys Tyr Arg Cys Glu Asn Gly Tyr Lys
            35                  40                  45

Ala Ser Ile Lys Gln Arg Asp Asn Gly Val Val Ser Ile Ala Phe Asn
        50                  55                  60

Asp Gly Lys Asp Ser Tyr Val Ser Tyr Leu Asn His Val Pro Ser Ala
65                  70                  75                  80

Ser Gly Thr Leu Tyr Val Asn Asp Lys Asn Thr Leu Lys Trp His Gln
                85                  90                  95

Lys Asn Asn Ile Ala Val Phe Thr Tyr Pro Asp Arg Asn Tyr Ala Lys
            100                 105                 110

Thr Gly Gln Leu Val Thr Thr Asn Cys His Lys Tyr
            115                 120
```